(12) United States Patent
Donahue (10) Patent No.: US 8,752,570 B2
(45) Date of Patent: Jun. 17, 2014

(54) VALVE FOR CONTROLLING THE FLOW OF STEAM AND OTHER FLUIDS

(75) Inventor: John Donahue, Kirkland, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/466,019

(22) Filed: May 7, 2012

(65) Prior Publication Data

US 2012/0216878 A1    Aug. 30, 2012

Related U.S. Application Data (63) Continuation of application No. 12/355,663, filed on Jan. 16, 2009, now Pat. No. 8,191,566, which is a continuation-in-part of application No. PCT/US2007/016428, filed on Jul. 20, 2007.

(60) Provisional application No. 60/832,446, filed on Jul. 21, 2006.

(51) Int. Cl.
*F16K 17/16* (2006.01)
*A61L 2/07* (2006.01)

(52) U.S. Cl.
USPC .......................... 137/68.23; 137/241; 422/26

(58) Field of Classification Search
CPC .......... F16K 17/16; F16K 17/162; A61L 2/07
USPC .......... 137/68.19, 68.23, 68.24, 68.25, 68.27; 251/4; 220/89.2; 422/26
See application file for complete search history.

(56) References Cited

U.S. PATENT DOCUMENTS

| | | | |
|---|---|---|---|
| 1,485,913 A | 3/1924 | Gottlieb | |
| 1,667,141 A | 4/1928 | Crowley | |
| 1,959,822 A | 5/1934 | Greve | |
| 2,092,925 A | 9/1937 | Lithgow | |
| 2,553,267 A | 5/1951 | Nedoh | |
| 2,764,173 A * | 9/1956 | Renner | 137/68.25 |
| 3,131,033 A | 4/1964 | Van Volkenburgh | |
| 3,445,032 A | 5/1969 | Raid, Jr. | |
| 3,845,879 A | 11/1974 | Dembach | |
| 3,881,629 A | 5/1975 | Shaw | |
| 4,064,003 A | 12/1977 | Newton | |

(Continued)

FOREIGN PATENT DOCUMENTS

| | | |
|---|---|---|
| WO | 03090843 A1 | 11/2003 |
| WO | 2008011132 A2 | 1/2008 |

OTHER PUBLICATIONS

Colder Products Company®, Steam-Thru Connections Features & Benefits webpage, 2005 <http://www.colder.com/asp_main/FeaturesBenefits/SteamThruFBBio.asp>, Mar. 6, 2006.

(Continued)

*Primary Examiner* — John Rivell
(74) *Attorney, Agent, or Firm* — Christensen O'Connor Johnson Kindness PLLC (57) ABSTRACT

A device for controlling fluid flow includes a conduit that defines a channel through which fluid flows opposing upstream and downstream directions of fluid flow. A rupture valve obliquely disposed in the channel to selectively prevent fluid flow through the channel, the rupture valve resisting rupture in response to pressure exerted on the rupture valve in the upstream direction and selectively rupturing in response to pressure exerted on the rupture valve in the downstream direction.

17 Claims, 6 Drawing Sheets

(56) References Cited

U.S. PATENT DOCUMENTS

| | | |
|---|---|---|
| 4,326,589 A * | 4/1982 | Ballman .................... 137/68.23 |
| 4,347,877 A | 9/1982 | Hoiss |
| 4,441,350 A | 4/1984 | Short, III |
| 4,458,516 A | 7/1984 | Naumann |
| 5,063,958 A | 11/1991 | Wisneskie |
| 5,167,337 A | 12/1992 | Short, III |
| 5,172,956 A | 12/1992 | Klose |
| 5,265,652 A | 11/1993 | Brunella |
| 5,411,158 A | 5/1995 | Kays |
| 6,192,914 B1 | 2/2001 | Farwell |
| 6,491,109 B2 | 12/2002 | Christenson |
| 6,983,758 B2 | 1/2006 | DeCourcy |
| 7,004,187 B2 | 2/2006 | Hoffman |
| 2002/0129858 A1 | 9/2002 | Meyer |
| 2005/0016620 A1 | 1/2005 | Proulx |

OTHER PUBLICATIONS

International Search Report, mailed Jul. 11, 2008, issued in corresponding International Application Serial No. PCT/US2007/016428, filed Jul. 20, 2007, 3 pages.

Millipore Catalogue—Lynx ST Connector for Steam-to Connection webpage, 2006 <http://www.millipore.com/ catalogue.nsf/docs/C9131>, Mar. 6, 2006.

Extended European Search Report mailed Aug. 2, 2013, issued in corresponding Application No. EP 07 810 635.8, filed Jul. 20, 2007, 6 pages.

* cited by examiner

VALVE FOR CONTROLLING THE FLOW OF STEAM AND OTHER FLUIDS

CROSS-REFERENCES TO RELATED APPLICATIONS

This application is a continuation of application Ser. No. 12/355,663, filed Jan. 16, 2009, which is a continuation-in-part of PCT Application No. PCT/US2007/016428, filed Jul. 20, 2007, which claims the benefit of Provisional Application No. 60/832,446, filed Jul. 21, 2006. These priority applications are incorporated herein by reference in their entireties.

BACKGROUND

Process vessels, such as bioreactors, may provide a closed environment for creating mixtures, performing chemical reactions, and/or growing biological cells, among others. For example, bioreactors often are employed to produce pharmaceuticals from engineered cells grown in many liters of culture media. In some cases, the cells placed into a bioreactor may be mammalian cells that grow more slowly than potential sources of contamination, such as bacteria and fungi. In any event, effective sterilization of a process vessel may be fundamental to the successful use of the process vessel without interference from unwanted microorganisms.

Small devices and vessels may be sterilized via gamma irradiation, autoclaving, or other means. Typically, larger process vessels and devices may be sterilized using "steam-in-place" (SIP) sterilization. This sterilization approach may involve connecting a process vessel to a steam source, such as via a conduit(s) and valve(s), to expose the interior volume and interior surfaces of the process vessel to the lethal effect of steam without the need to move the process vessel. Furthermore, the sterilization may be performed repeatedly as different fluid sources are connected to the process vessel. However, the conduit(s) and valve(s) used in connecting the fluid sources may require cleaning and/or re-sterilization between uses, which may be costly and time consuming. Accordingly, new approaches for transferring fluids from fluid sources to process vessels would be beneficial.

SUMMARY

A first embodiment of a disclosed device for controlling fluid flow includes a conduit that defines a channel with opposing upstream and downstream directions of fluid flow. A rupture valve is obliquely disposed within the channel to selectively prevent fluid flow through the channel. When pressure is exerted on the rupture valve in the upstream direction, the rupture valve resists rupture. When pressure is exerted on the rupture valve in the downstream direction, the rupture valve selectively ruptures.

A second embodiment of a disclosed device for controlling fluid flow includes a conduit having opposing upstream and downstream directions of fluid flow. A rupture valve is disposed within the conduit to selectively restrict fluid flow through the conduit. The rupture valve includes a rupturable element and a support element connected to the rupturable element. The support element supports the rupturable element against rupture in response to pressure on the rupture valve exerted in an upstream direction. The support element pivots with the rupturable element to permit fluid flow through the channel after the rupturable element ruptures selectively in response to pressure exerted in a downstream direction.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The present teachings provide systems (e.g., bioprocessing systems), including methods and apparatus, with fluid flow regulated by a rupture valve. In some embodiments, the rupture valve may restrict fluid flow to maintain sterility upstream and/or downstream of the rupture valve.

The apparatus may include a conduit assembly with a conduit occluded by a rupture valve. The rupture valve may operate substantially like a single-use check valve that opens (ruptures) selectively in response to pressure exerted in one of two opposing (potential) flow directions through the conduit. Accordingly, the rupture valve may restrict fluid flow in an upstream direction through the conduit, such as during steam-in-place sterilization downstream of the rupture valve. In addition, the rupture valve may rupture after sterilization, in response to pressure on the rupture valve directed downstream, to permit fluid flow through the site of sterilization downstream of the rupture valve, such as for addition of a fluid reagent(s) to a connected downstream receiver (e.g., a reaction chamber of a bioreactor). In some embodiments, the rupture valve may be disposed obliquely in the conduit. An oblique disposition of a rupture valve may, in some cases, facilitate removal of steam condensate from the conduit assembly in both horizontal and vertical orientations of the assembly. In some embodiments, the rupture valve may include a rupturable occlusion element and a support element connected in a face-to-face relationship with one another. The support element may support the rupturable element during the exertion of upstream-directed pressure on the rupture valve (such as during application of steam), and then may pivot with the rupturable element when the rupturable element bursts.

The apparatus may be attached to an upstream (and/or downstream) device such as a capsule filter, tubing assembly, or small vessel, among others, and sterilized with the upstream device (e.g., via gamma-irradiation, autoclaving, etc.). The rupture valve in its intact form may ensure that the upstream device remains sterile prior to use and/or prior to connection to a process vessel. Accordingly, the rupture valve may allow an upstream device to be connected aseptically to a process vessel.

The methods may be used for performing in-place sterilization followed by fluid transfer. For example, the methods may include (1) applying a sterilizing agent, such as steam, selectively to an outlet portion of the conduit assembly while the rupture valve restricts entry of the sterilizing agent into an inlet portion of the conduit assembly, and (2) rupturing the rupture valve such that fluid (e.g., a fluid reagent(s)) can flow into the outlet portion from an inlet portion of the conduit assembly.

Overall, the systems of the present teachings may provide substantial advantages over other systems employing more complicated mechanical valves for maintaining sterility and regulating fluid flow before, during, and/or after sterilization in-place. These advantages may include, for example, greater flow rates, disposability, lower overall cost, and/or reduced microbial contamination, among others.

Further aspects of the present teachings are described in the following sections, including, (I) overview of an exemplary bioprocessing system; (II) conduit assemblies, including (A) conduits, (B) rupture valves, (C) and drains; (III) methods of making conduit assemblies with rupture valves; (IV) methods of using rupture valves; and (V) examples.

I. OVERVIEW OF AN EXEMPLARY BIOPROCESSING SYSTEM

The rupture valves of the present teachings may be used in any suitable system in which fluid is being transferred within, into, and/or out of the system. In particular, the rupture valves may be appropriate for systems that benefit from sterile conditions, such as bioprocessing systems. This section describes exemplary configurations of a bioprocessing system with a rupture valve.

Figure 1:
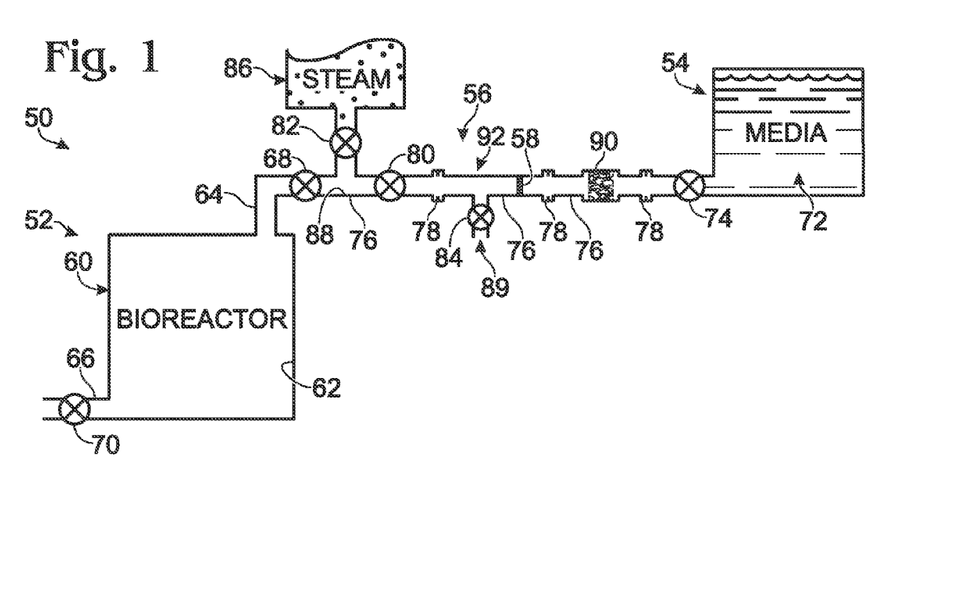
FIG. 1 is a schematic view of an exemplary bioprocessing system including a rupture valve, in accordance with aspects of the present teachings.

FIG. 1 shows an exemplary bioprocessing system 50. System 50 may include a downstream receiver vessel 52 connected to an upstream supply vessel 54 by a fluid conduction subsystem (an addition assembly) 56 that includes at least one rupture valve 58. The rupture valve may regulate fluid flow through the conduction subsystem by, for example, restricting reverse (upstream) flow (receiver vessel 52 to supply vessel 54) during sterilization and permitting forward (downstream) flow (supply vessel 54 to receiver vessel 52) afterwards. More generally, the rupture valve may remain closed (resist rupture) with a substantial pressure drop directed upstream on the rupture valve and may open (rupture) with the same substantial pressure drop directed downstream on the rupture valve.

The receiver vessel may be a process vessel for performing bioprocessing, such as growth of cells, production of biological products, enzymatic reactions, and/or the like. Accordingly, the receiver vessel may be a closed container (here, a bioreactor 60) defining a reaction chamber 62. In addition, the receiver vessel may have an inlet region(s) 64 at which the receiver vessel connects to the fluid conduction subsystem and an outlet region(s) 66 for removing fluid from the bioreactor (such as during and/or after bioprocessing and/or to remove steam condensate (see below)). Fluid entry into and/or out of the receiver vessel may be controlled by valves, such as an inlet valve 68 and an outlet valve 70, respectively.

Source vessel 54 may serve as a fluid source that holds a fluid reagent 72 (here, media) prior to delivery of the fluid reagent to the fluid conduction subsystem and then the bioreactor. The source vessel may be open, or may be a closed container as shown here. Entry of the fluid reagent into fluid conduction subsystem 56 may be regulated by an outlet valve 74, may be facilitated by a vent, and/or may be driven by a pump, among others.

Fluid conduction subsystem 56 may direct and regulate the flow of fluid between the source vessel and the receiver vessel. Subsystem 56 thus may include one or more conduits 76, connected to one another and/or to the supply and/or receiver vessels via couplings 78, and one or more in-line valves 80 and/or branch valves 82, 84. The branch valves may be used to introduce fluid into and/or out of the conduction subsystem. For example, valve 82 may be configured to regulate fluid communication between a steam source 86 and a main channel 88 of the conduction subsystem, for application of steam to the main channel and/or bioreactor. In contrast, drain valve 84 (also termed a bleed valve) may provide removal of fluid from the system via a drain 89, such as removal of condensate that accumulates during steam sterilization.

The fluid conduction subsystem also may alter and/or sense fluid as it travels through the conduction subsystem. For example, the conduction subsystem may have a filter 90 and/or other fluid modification and/or sensing devices (such as mixers, heaters, coolers, degassers, electrodes, temperature sensors, flow sensors, fluid sensors, pH sensors, position sensors, and/or the like).

Rupture valve 58 may be included in the bioprocessing system as part of a conduit assembly 92. The conduit assembly may form part of the main channel of the fluid conduction subsystem and thus may have coupling structures 78 that permit the conduit assembly to be integrated into the conduction subsystem. In addition, the conduit assembly may include drain valve 84, filter 90, and/or other accessory devices, structures, and/or features as described elsewhere in the present teachings. Filter 90 and rupture valve 58 (and any suitable portion of fluid conduction subsystem 56) may be connected (or formed as a unit) and then sterilized as a unit via autoclaving, gamma irradiation, or other suitable means prior to incorporating the unit into the system. In other embodiments, upstream vessel 54, an intervening portion of fluid conduction subsystem 56, and rupture valve 58 (with or without filter 90) may be connected (or formed as a unit) and then sterilized as a unit via autoclaving, gamma irradiation, or other suitable means prior to incorporating the unit into the system. Further structural aspects of conduit assemblies are described below, for example, in Sections II and V.

Figure 2:
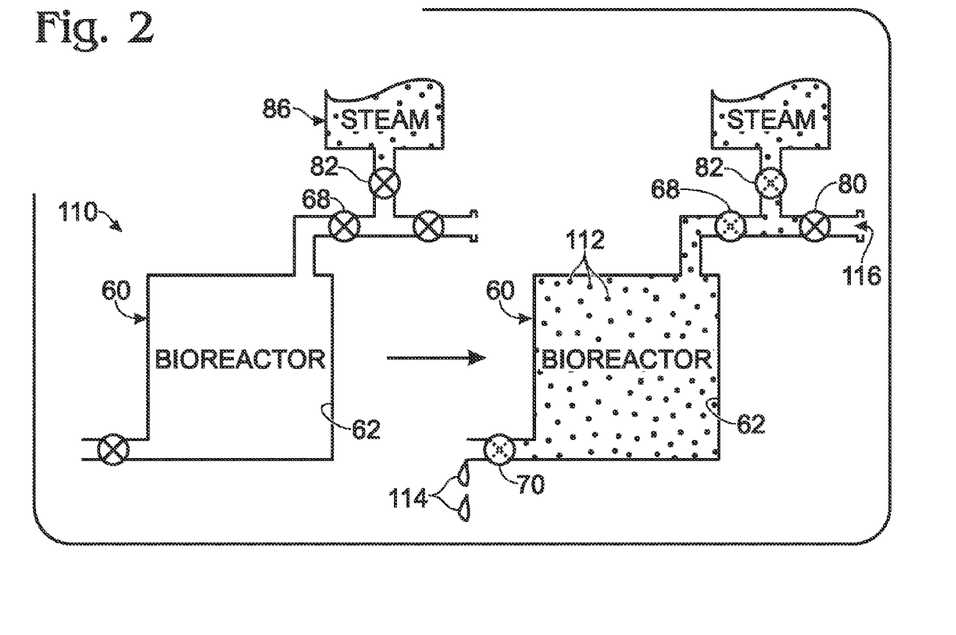
FIG. 2 is a flow diagram illustrating steam-in-place sterilization of a reaction chamber of the bioprocessing system of FIG. 1 before connection of the reaction chamber to the rupture valve, in accordance with aspects of the present teachings.

FIG. 2 shows a flow diagram 110 illustrating steam-in-place sterilization of reaction chamber 62 of bioreactor 60 before connection of the reaction chamber to fluid conduction subsystem 56 and source vessel 54 (see FIG. 1). On the left, the bioreactor is connected to steam source 86 but is isolated from the steam source by inlet valve 68 and steam valve 82. On the right, valves 68 and 82 are open (indicated by a dashed "X" in each valve) and steam 112 is in reaction chamber 62. Outlet valve 70 also may be open, to function as a drain valve that permits removal of condensate 114 from the reaction chamber. (Generally, steam sterilization may be more effective when condensed steam is removed from the chamber (and/or from a conduit(s)) so that condensate does not shield surfaces from steam contact.). However, here, main channel valve 80 isolates the reaction chamber from a nonsterile port 116 to which the remaining portions of the fluid conduction subsystem will be connected (see below).

Figure 3:
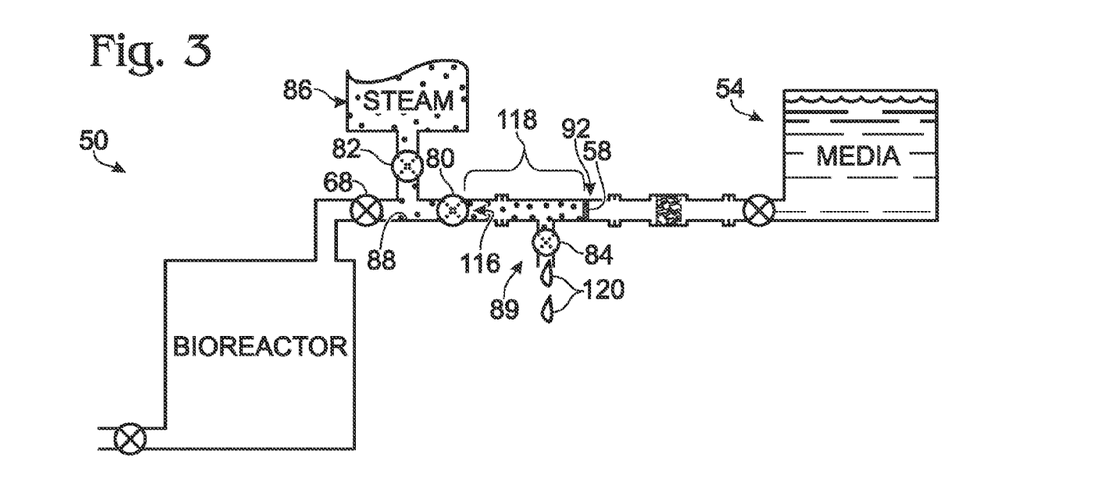
FIG. 3 is a schematic view of the bioprocessing system of FIG. 1 taken as in FIG. 1 during steam-in-place sterilization of an isolated channel of the bioprocessing system disposed between the reaction chamber and the rupture valve, in accordance with aspects of the present teachings.

FIG. 3 shows the steam-sterilized bioreactor of FIG. 2 connected to fluid source 54 via main channel 88. A channel region 118 defined between channel valve 80 and rupture valve 58 may be nonsterile when conduit assembly 92 is coupled to port 116. Accordingly, channel region 118 may be sterilized by selective application of steam from steam source 86 to this portion of the main channel. In particular, steam valve 82 and channel valve 80 may be opened to permit steam to pass from the steam source into channel region 118. Inlet valve 68 may open to permit concurrent sterilization of the bioreactor (e.g., if not yet sterile) or may remain closed during this process to keep the bioreactor isolated from the steam (e.g., to keep the sterilization process more efficient and/or to protect steam-sensitive material that may already have been added to the bioreactor). Channel region 118 may be isolated at the other end via rupture valve 58, as described in more detail in the examples of Section V. Steam condensate 120 may be removed during the steam sterilization process using drain 89 by opening drain valve 84.

Figure 4:
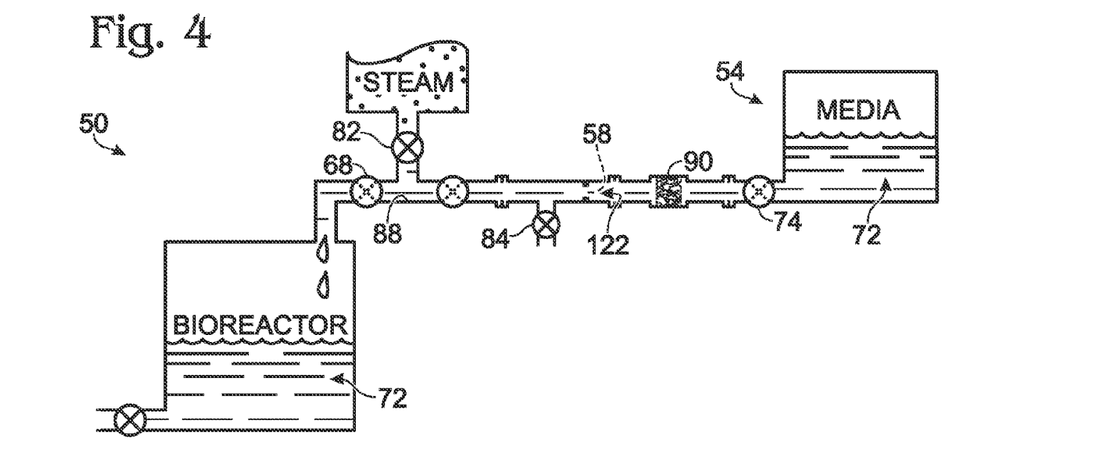
FIG. 4 is a schematic view of the bioprocessing system of FIG. 1, taken as in FIG. 1 after opening of the rupture valve and during addition of a fluid reagent to the reaction chamber through a filter and through a passageway created by valve opening, in accordance with aspects of the present teachings.

FIG. 4 shows bioprocessing system 50 during addition of a fluid reagent from fluid source 54, after steam sterilization of channel region 118 (see FIG. 3) has been completed. Steam valve 82 has been closed to shut off the steam, and drain valve 84 also has been closed. In contrast, inlet valve 68 of the bioreactor and outlet valve 74 of fluid supply 54 have been opened. Fluid reagent 72 may travel through main channel 88 due to rupture of rupture valve 58, which created a passageway 122 through which the fluid reagent may flow. In FIG. 3, the rupture valve resisted rupture when pressure was exerted in an upstream direction (by steam). However, here, the rupture valve ruptured in response to pressure exerted by the fluid supply in a downstream direction. The fluid reagent may be filtered as it passes through filter 90, such as to sterilize the fluid reagent, and/or may be added to the bioreactor without filtration (e.g., if the fluid reagent is presterilized or should not be sterilized). Further aspects of using rupture valves to regulate fluid flow are described elsewhere in the present teachings, such as in Sections IV and V, among others.

II. CONDUIT ASSEMBLIES

The fluid transfer systems of the present teachings may include one or more conduit assemblies for regulating the flow of fluid within a system. Each conduit assembly may have any suitable structure, particularly a structure selected according to the transfer system for which the conduit assembly is to be used.

The conduit assembly may be packaged in a sterile condition. Accordingly, the conduit assembly may be treated, before or after packaging, with a sterilizing agent that kill microorganisms. The sterilizing agent may be, for example, electromagnetic radiation (e.g., gamma, UV, and/or microwave radiation, among others), heat (e.g., via treatment with steam), a toxic gas (e.g., ethylene oxide), a toxic liquid solution (e.g., formaldehyde and/or hydrogen peroxide), and/or the like. In some examples, exposure of the conduit assembly to radiation may be more suitable because the radiation may be capable of penetrating a sealed package, to allow sterilization of the conduit assembly within the sealed package.

The conduit assembly may have any suitable devices, structures, and features, assembled in any suitable manner, as appropriate. Generally, each conduit assembly has one or more conduits and at least one rupture valve regulating fluid flow through at least one of the conduits. The conduit assembly also may have one or more additional (non-rupture) valves arranged in series or in parallel with the rupture valve(s). These additional valves may include a side valve that regulates fluid flow through a side channel and/or an in-line or main valve that regulates fluid flow through a main channel in which the rupture valve is disposed. In addition, the conduit assembly may include one or more filters (e.g., small-pore filters for removal of microorganisms), one or more chambers or containers for holding fluid, one or more sensors (e.g., any of the sensors described above in Section I), a pump (e.g., powered manually or electrically, among others) to drive fluid through the conduit assembly, and/or the like. Further aspects of conduit assemblies are described elsewhere in the present teachings and below in the following subsections (A) conduits, (B) rupture valves, and (C) drain valves.

A. Conduits

A conduit assembly may have at least one conduit for channeling fluid through the conduit assembly. The conduit may have any suitable shape and size according to the intended purpose of the conduit assembly.

The conduit (and/or a body tube thereof) may have any suitable shape. For example, for primary flow through the conduit, the conduit may define a main channel that is linear or bent (i.e., curved and/or bent angularly in two or three dimensions). The conduit may be elongate, with a length (measured in the direction(s) of fluid flow) that is substantially greater than the diameter (measured in a direction transverse to fluid flow). Alternatively, in some examples, the conduit length may be about the same as or less than its diameter. The diameter of the conduit may be substantially uniform or may be nonuniform along the length of the conduit. If nonuniform, the conduit may taper and/or flare generally from inlet end to outlet end, from inlet end to rupture valve, and/or from rupture valve to outlet end, among others. A tapered/flared conduit may be suitable in some cases to provide an end region (e.g., a coupling structure) that is larger or smaller in area than the rupture valve. Alternatively, or in addition, the conduit may widen (or narrow) in an intermediate portion of its length to accommodate an internal device, such as a filter, a sensor, a pump, another valve, and/or the like. The conduit may have any suitable cross-sectional shape, such as circular, oval (with a pair of linear sides), elliptical, polygonal, rosette, and/or the like. In addition, the cross-sectional shape may be substantially the same along the length of the conduit or may be different at two or more positions along the length.

The conduit may be unbranched, to define a single flow path through the conduit, or may be branched, to define alternative flow paths through the conduit. If branched, the conduit may branch any suitable number of times and at any suitable positions in the conduit. For example, the conduit may branch upstream of the rupture valve. An upstream branch may create two or more discrete inlets for the conduit assembly, such as for serial and/or parallel flow of fluid through the rupture valve from two or more fluid sources connected to the conduit assembly. Alternatively, one of the upstream branches may offer an alternative path (e.g., between vessels) that bypasses the rupture valve. Alternatively, or in addition, the conduit may branch downstream of the rupture valve. A downstream branch may create two or more discrete outlets for the conduit assembly, such as for flow of fluid to two or more receiver vessels and/or for alternative flow to either a receiver vessel or to a drain valve. Branched conduits may define branch channels of similar or different sizes. For example, a conduit with an upstream (or downstream) branch may define discrete inlets (or outlets) of about the same cross-sectional area for carrying fluid from different fluid sources (or to different destinations) at about the same flow rate, everything else being equal. In contrast, a conduit with a downstream (or upstream) branch may define discrete outlets (or inlets) of different cross-sectional areas for carrying fluid to different destinations (or from different sources) at different flow rates, everything else being equal.

The conduit may have any suitable size. The length of the conduit generally should be sufficient to allow incorporation of a rupture valve along the length and, optionally, to a form a coupling structure(s), such as at one or both opposing ends of a body tube of a conduit. However, the length may be extended, as appropriate, to facilitate handling and use, such as a longer conduit to make connections to more widely spaced connection sites. The conduit may have any suitable diameter, generally according to a desired flow rate and/or transfer volume of fluid through the conduit. In particular, the conduit may have a substantially larger diameter and thus a substantially greater flow (and volume transfer) rate than conduits in valves, such as diaphragm valves, used for corresponding fluid transfer applications. For example, in some cases, the conduit may have a diameter of about 0.5 to 10 cm, to accommodate a corresponding range of flow rates and volumes of fluid to be transferred. In some embodiments, the diameter of the conduit may be different after the conduit branches, as described above.

The conduit may have any suitable average wall thickness, generally selected according to the size, composition, and desired strength of the conduit. The wall thickness may be generally uniform or nonuniform along and/or around the conduit. For example, the wall thickness may be thicker adjacent an end(s) of the conduit, to provide a site and/or strength for coupling, and/or may vary to form projections and/or recesses in the outer and/or inner surface(s) of the wall. In some embodiments, the wall may define one or more openings (e.g., through-holes) intermediate the ends of the conduit. The opening(s) may be disposed upstream of the rupture valve, downstream of the rupture valve, or both.

B. Rupture Valves

Each conduit assembly may include at least one rupture valve disposed in a channel defined by the conduit assembly. The rupture valve may be any valve that is breached by bursting open, generally irreversibly. Accordingly, the rupture valve may be open permanently after it has ruptured and thus may be a single-use valve suitable for only one use.

The rupture valve may be breached by structural damage to a portion of the valve, generally a rupturable element (an occlusion element) that partially or completely occludes the channel of the conduit assembly. The structural damage may be tearing or breaking of the rupturable element as fluid breaches the element. Alternatively, or in addition, the structural damage may include cutting the rupturable element with a sharp point or sharp edge that engages the rupturable element. In some embodiments, the rupture valve thus may be associated with a cutting mechanism that is actuated by downstream-directed pressure on the cutting mechanism and/or rupture valve. The cutting mechanism may initiate rupture of the rupturable element, which may be continued as, for example, a tearing action produced by fluid pressure.

The rupture valve may be breached at a predefined rupture region of the rupture valve. The predefined rupture region may have any suitable shape, size, position, and structure in rupturable element of the rupture valve.

The shape of the predefined rupture region, as viewed orthogonally to a face of the rupturable element, may be U-shaped, V-shaped, C-shaped, J-shaped, circular, oval, elliptical, polygonal, and/or a combination thereof, among others. The predefined rupture region may define an uninterrupted path or may be comprised of a plurality of discrete segments that are spaced from one another. In addition, the predefined rupture region may extend along and/or around a closed loop (s) or an open loop(s), among others. Furthermore, the predefined rupture region may be shaped to maximize the flow rate through the rupture valve after rupture. Accordingly, the predefined rupture region may be designed as a compromise between the size of opening produced by rupture and the angle of flexion permitted by the size/shape of the predefined rupture region in conjunction with its proximity to conduit walls.

The predefined rupture region may have any suitable size and position in relation to a corresponding rupturable element and/or conduit. For example, the predefined rupture region may define a shape with a diameter that is slightly less than or substantially less than the diameter of the rupturable element. In addition, the diameter of the predefined rupture region may be about the same as (although generally slightly less than)

the inner diameter of a corresponding conduit, such that the predefined rupture region is disposed near to the inner surface of the conduit. However, in some examples, the predefined rupture region may be spaced (radially inward) from the inner surface of the conduit, so that the predefined rupture region can be supported by a support element of the rupture valve that extends radially inward from the conduit inner surface (e.g., see Examples 1 and 2). The predefined rupture region may have any suitable depth relative to the thickness of a corresponding rupturable element. For example, the predefined rupture region may be less than, at least about one-half, or substantially greater than one-half the thickness. In some embodiments, the predefined rupture region may be a structurally weakened portion of the rupturable element that is created without reducing the thickness of the rupturable element. For example, the rupturable element may be weakened locally via treatment with light (e.g., a laser), heat, pressure (e.g., bending), and/or the like. The predefined rupture region may occupy any suitable portion of the area of a rupturable element, although generally substantially less than one half.

The rupture valve may be configured to have any suitable resistance to upstream-directed pressure and any suitable sensitivity to downstream-directed pressure. Generally, the rupture valve may be capable of withstanding upstream-directed pressure that is substantially greater than atmospheric pressure, for example, at least about 50% more than, or at least about twice or three times atmospheric pressure. In addition, the rupture valve may be configured to withstand relatively small downstream-directed pressures, to avoid inadvertent rupture of the rupture valve created by premature pressure fluctuations prior to fluid addition from an upstream fluid source. Furthermore, the rupture valve may be configured to rupture in response to any suitable increased pressure created by the upstream fluid source. The rupture characteristics of the rupture valve may be selected based on the material and thickness of the rupturable element, the size and shape of the predefined rupture region in the rupturable element, the position of the predefined rupture region, the position of a support element relative to the rupturable element/predefined rupture region, and/or the inner diameter of the conduit, among others.

The rupture valve may have any suitable longitudinal and angular disposition in a conduit assembly. For example, the rupture valve may be disposed generally centrally along the length of a conduit of the assembly. Alternatively, or in addition (in the case of a plurality of rupture valves), the rupture valve may be disposed near an end of the conduit. In addition, the rupture valve may be disposed orthogonally in the conduit (e.g., defining a plane that is orthogonal to a primary flow axis of the conduit and see Example 3) or may be disposed obliquely (e.g., see Examples 1, 2, 4, and 5).

C. Drains

A conduit assembly may have one or more drains (also termed steam access ports) for removing fluid laterally from the conduit assembly. Each drain may include a drain conduit and one or more valves (termed drain valves or bleed valves) for regulating fluid movement through the drain conduit. The one or more valves may be arranged in parallel or in series relative to one another.

A drain valve may have any suitable structure and mechanism of operation. Accordingly, the drain valve may be, for example, an angle, ball, butterfly, diaphragm, flapper, gate, globe, needle, pinch, slide, stopcock, and/or thumbscrew valve, among others. The drain valve may be driven and/or controlled (e.g., opened, closed, or adjusted at selected times) manually and/or according to a threshold or change in temperature, pressure, presence/absence of fluid, and/or the like. The temperature, pressure, presence/absence of fluid, etc. may be sensed mechanically or electronically, among others. In some embodiments, a drain valve may function as a check valve (such as in a steam trap) that opens selectively to release liquid water and closes to retain steam.

The drain valve may control flow through a drain channel of any suitable size. The drain channel may have about the same cross-sectional area as a main channel of the conduit assembly or may be substantially smaller in cross-sectional area.

III. METHODS OF MAKING CONDUIT ASSEMBLIES WITH RUPTURE VALVES

The rupture valves of the present teachings may be fabricated, generally as part of conduit assemblies, by any suitable methods. The methods may use any suitable number of components, components of any suitable composition(s), and components connected to one another by any suitable connection mechanism(s).

A conduit assembly may be assembled from any suitable number of components. For example, the conduit assembly may be assembled using a discrete component(s) that forms or contributes to the rupture valve (e.g., a rupturable element thereof) and one or more other discrete components that form the conduit (e.g., see Examples 2-4). Alternatively, the conduit assembly may have at least part of the conduit and part of the rupture valve formed by the same component (e.g., see Example 1).

A conduit assembly may have any suitable composition. Generally, however, the conduit assembly (or at least an outlet thereof) may have a composition that is capable of withstanding exposure to steam without substantial warping or melting. In exemplary embodiments, at least a portion of the conduit assembly may be constructed of steam-resistant plastic. The components of a conduit assembly may be formed of the same material or of different materials. For example, the conduit may be formed of a harder, stronger plastic; a support element of the rupture valve also may be formed of a harder, stronger plastic; and a rupturable element of the rupture valve may be formed of a softer, weaker plastic. In some examples, at least a portion of the conduit may be formed of a more flexible material, such that the conduit assembly may be bendable to facilitate connection of the conduit assembly to upstream and/or downstream connection sites.

The components of a conduit assembly may be connected to one another by any suitable mechanism(s). Exemplary mechanisms may include an adhesive, welding, bonding, an interference fit, a fastener(s), and/or the like.

IV. METHODS OF USING RUPTURE VALVES

The rupture valves of the present teachings may be used in any suitable fluid transfer operations for any suitable purpose. An exemplary method of using rupture valves is presented here. The method steps listed may be performed in any suitable order, in any suitable combination, and any suitable number of times.

A conduit assembly may be selected. The conduit assembly may include a conduit and a rupture valve. The conduit may define a channel, and the rupture valve may divide the channel into an inlet portion (an upstream portion) and an outlet portion (a downstream portion). The rupture valve may be rupturable selectively in response to pressure exerted in a downstream direction on the rupture valve. The conduit assembly may include any of the components, structures, and/or features described in the present teachings. The conduit assembly may be sterilized by any of the treatments described elsewhere in the present teachings. Sterilization of the conduit assembly may be performed before (and/or after) the conduit assembly is connected to a downstream receiver, such as a conduit and/or process vessel. Furthermore, sterilization the conduit assembly may be performed after (and/or before) the conduit assembly is connected to an upstream device, conduit, and/or vessel.

A sterilizing agent may be applied selectively to the outlet portion of the conduit assembly, for example, after the conduit assembly has been connected to a downstream receiver, such as a downstream conduit and/or process vessel. The sterilizing agent may be any of the agents described herein, for example, steam. The rupture valve may restrict entry of the sterilizing agent into the inlet portion of the conduit assembly by resisting rupture during application of the sterilizing agent. If steam is used as the sterilizing agent, the steam may have a suitable temperature and pressure for killing microorganisms. In addition, application of the steam (or other sterilizing agent) may be performed over a time period (in conjunction with the steam temperature and pressure) that is sufficient, to "sterilize" the outlet portion of the conduit assembly. The terms "sterilize" and "sterilization," as used herein, refer to a process or procedure that results in, or would be expected to result in, a substantial reduction in microorganism viability. The substantial reduction may be described as a "log kill" of any suitable magnitude, such as a one-log kill (i.e., a tenfold reduction in viability), a two-log kill, a three-log kill, a six-log kill, and/or the like. Similarly, the term "sterile" is intended to mean a condition of substantially reduced microorganism viability produced by sterilizing or sterilization.

A drain valve of the conduit assembly (or a valve spaced from the conduit assembly but in fluid communication therewith) may be opened before and/or during application of the sterilizing agent. Opening of the drain valve may be performed manually or automatically. Furthermore, the drain valve may be opened only once, before or during application of the sterilizing agent, or may be opened repeatedly.

The rupture valve may be ruptured after the step of applying, with pressure exerted in a downstream direction from the inlet portion. The pressure may be exerted by upstream fluid. For example, pressure may be exerted directly by a fluid reagent from an upstream fluid source. Alternatively, the pressure may be exerted indirectly by the fluid reagent, such as via gas that is disposed downstream of the fluid reagent in the inlet portion.

Any suitable fluid reagent(s) may flow through the (breached) rupture valve for transfer of the fluid reagent to a downstream site. The fluid reagent may be substantially liquid, such as water, an aqueous solution/mixture, a buffer, a suspension of particles (e.g., cells) in a liquid, a growth medium, a non-aqueous liquid or mixture, and/or the like. Alternatively, or in addition, the fluid reagent may be substantially gas, a gas mixture, and/or the like. In addition, any suitable volume of the fluid reagent may flow through the rupture valve, such as at least about one or 100 L, among others. In some embodiments, the volume may be at least about 1,000 L, or may be up to about 100,000 L, or more.

The fluid reagent may flow to any suitable destination. Exemplary destinations may include a discrete downstream conduit, a chamber (such as a bioreactor chamber), a vial, a microplate, etc. The destination may be in a sterile condition (at least interiorly) or may be nonsterile.

A breached rupture valve may be used for fluid transfer from and to any suitable number of fluid sources and fluid destinations. Two or more fluid transfers may be performed in series, such as by serially connecting different fluid sources and/or different receiver vessels to the same conduit assembly. Alternatively, or in addition, two or more fluid transfers may be performed in parallel, such as by using a conduit assembly with a branched conduit structure that allows concurrent connection to two or more fluid sources and/or two or more receiver vessels.

V. EXAMPLES

The following examples describe selected aspects and embodiments of the present teachings, particularly exemplary conduit assemblies and methods of using the conduit assemblies to regulate fluid flow and/or transfer fluid. These examples and the various features and aspects thereof are included for illustration and are not intended to define or limit the entire scope of the present teachings.

Example 1

Conduit Assembly with Oblique Rupture Valve

This example describes an exemplary conduit assembly 140 including a conduit and a rupture valve with an oblique disposition within the conduit; see FIGS. 5-11.

Figure 5:
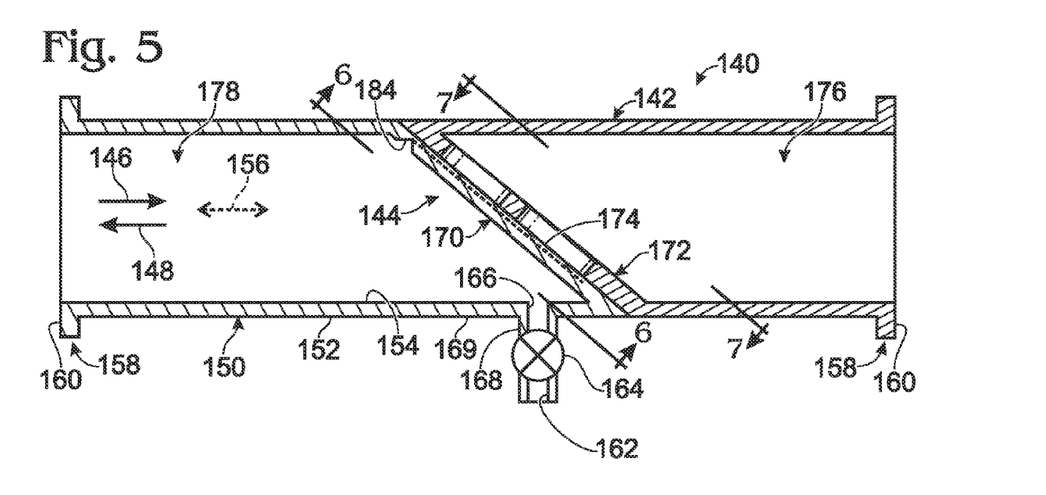
FIG. 5 is a longitudinal sectional view of an exemplary conduit assembly including a rupture valve disposed obliquely, in accordance with aspects of the present teachings.

FIG. 5 shows a longitudinal sectional view of conduit assembly 140. The conduit assembly may include a conduit 142 and a rupture valve 144 that regulates fluid flow through the conduit.

Conduit 142 may be structured to define opposing directions of (potential) flow, namely, upstream direction 146 and downstream direction 148. The conduit thus may have a body or body tube 150 having an outer wall 152 defining a main or longitudinal channel 154, which may extend parallel to a long axis 156 of the conduit. The body tube may be a hollow cylinder or may have any other suitable shape (see Section II above).

The conduit also may have any other suitable structures. For example, the conduit may have opposing end regions 158 that provide coupling structures, such as flanges 160, for making sealed connections to other conduits and/or vessels. The flanges may extend radially outward of wall 152 of the body tube in a circumferential arrangement to provide structure suitable for engagement with a clamp (such as a tri-clamp fitting to be secured by a tri-clamp). The conduit also may define a side or ancillary channel 162 connected to a side or drain valve 164 to create a drain. Accordingly, the body tube of the conduit may define an opening 166 in wall 152 that communicates with the drain. Furthermore, ancillary channel 162 may be defined by an ancillary conduit 168 that projects laterally from a main conduit 169, such that conduit 142 is branched.

Rupture valve 144 may be structured asymmetrically for differential sensitivity to pressure exerted in the opposing directions of flow 146, 148. In particular, the rupture valve may have a rupturable element (an occlusion element) 170 that occludes main channel 154, and a support element (e.g., a backing plate) 172 disposed adjacent the rupturable element, for example, adjacent an upstream face 174 of the rupturable element. The rupture valve thus may divide main channel 154 into an inlet portion 176 and an outlet portion 178, and the support element may be adjacent the inlet portion.

The rupturable element (and, optionally, the perimeter the support element) may extend circumferentially to outer wall 152 of the conduit, to provide a sealed relationship with the outer wall that blocks fluid flow through the conduit. Accordingly, the rupturable element may be structured as a disc. Here, the rupturable element (and the rupture valve and the support element) has an oblique orientation relative to the conduit, that is, the rupturable element defines a plane disposed obliquely relative to the conduit and/or relative to a long axis thereof.

Conduit assembly 140 may have any suitable number of pieces formed and connected by any suitable approach. In some examples, the conduit assembly may have rupture valve 144 and body tube 150 formed by only two components, namely, an upstream component and a downstream component, as shown here. Ancillary conduit 168 may be unitary with the downstream component or may be a separate component that is attached to the downstream component. Similarly, flanges 160 may be unitary with their respective upstream and downstream components or may be formed separately and attached to the components.

Figure 6:
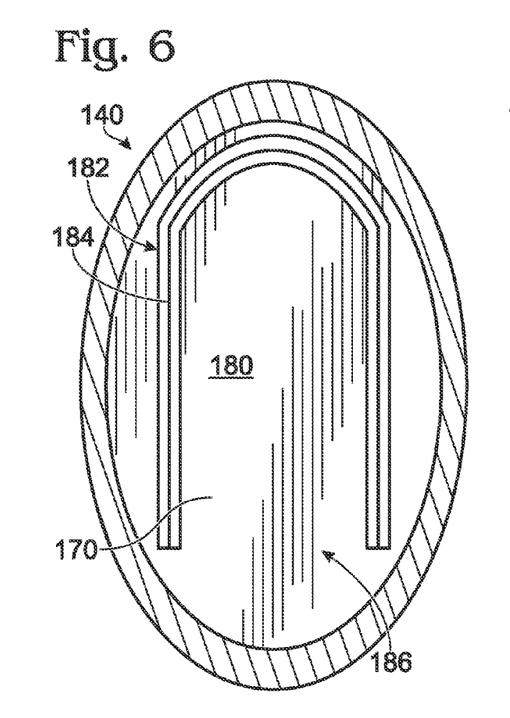
FIG. 6 is a cross-sectional view of the conduit assembly of FIG. 5, taken generally along line 6-6 of FIG. 5 from an outlet (downstream) side of the rupture valve.

FIG. 6 shows a cross-sectional view of conduit assembly 140 taken from outlet portion 178 (see FIG. 5), toward a downstream face 180 of rupturable element 170. The rupturable element may be structured such that a predefined region 182 of the rupturable element tears and/or fractures when the rupturable element ruptures. The predefined region may be structurally weaker than other portions of the rupturable element. For example, the rupturable element may be fabricated and/or pre-cut (e.g., scored) to form a groove or slit in one or both opposing faces of the rupturable element. Here, the downstream face of the rupturable element has a generally U-shaped groove 184 extending adjacent a majority of the perimeter of the rupturable element (see FIG. 5 also). The groove (or other structurally weakened region) may extend in a closed loop or may extend in an open loop configuration, as shown here, among others. In any case, the groove (or other weakened region) may terminate or may be shallower (and/or less weak) along a portion of a circumferential path to form a hinge region 186 at which the rupturable element may flex without tearing/fracturing. This structural arrangement may provide a rupturable element that ruptures efficiently and flexes (e.g., pivots) to move out of the flow path (i.e., dispose its opposing faces parallel to the flow path), without detaching completely from the conduit assembly.

Figure 7:
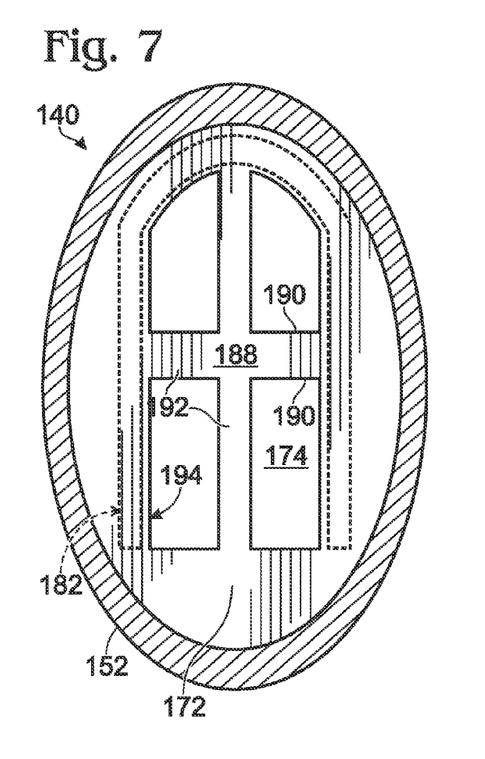
FIG. 7 is a cross-sectional view of the conduit assembly of FIG. 5, taken generally along line 7-7 of FIG. 5 from an inlet (upstream) side of the rupture valve.

FIG. 7 shows a cross-sectional view of conduit assembly 140 taken from inlet portion 176 (see FIG. 5), toward an upstream face 188 of support element 172 (and toward upstream face 174 of rupturable element 170). Support element 172 may define one or more openings 190 for fluid flow through the conduit after rupture of the rupturable element. For example, the support element may define a plurality of openings separated by brace elements 192 that support the rupturable element centrally. The support element also or alternatively may support the rupturable element laterally, for example, extending inward, indicated at 194, from outer wall 152 of the conduit to overlap and/or extend beyond and support predefined rupture region 182.

Figure 8:
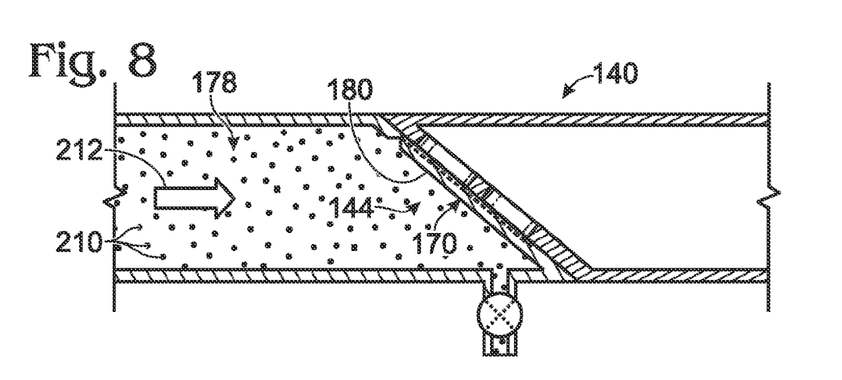
FIG. 8 is a fragmentary, longitudinal sectional view of the conduit assembly of FIG. 5 taken during selective application of steam to an outlet portion of the conduit assembly, in accordance with aspects of the present teachings.

FIG. 8 shows conduit assembly 140 during application of steam 210 to outlet portion 178. The steam is exerting a pressure, indicated by an open arrow at 212, on rupture valve 144, via contact with upstream face 180 of rupturable element 170. The term "pressure," as used herein, means a net positive pressure. Accordingly, here, the steam creates a pressure drop directed upstream in the conduit assembly through the rupture valve. In this configuration, the rupturable element resists rupture because the support element restricts upstream movement of the rupturable element that otherwise may promote tearing/fracture at the predefined rupture region of the rupturable element (see FIG. 6).

Figure 9:
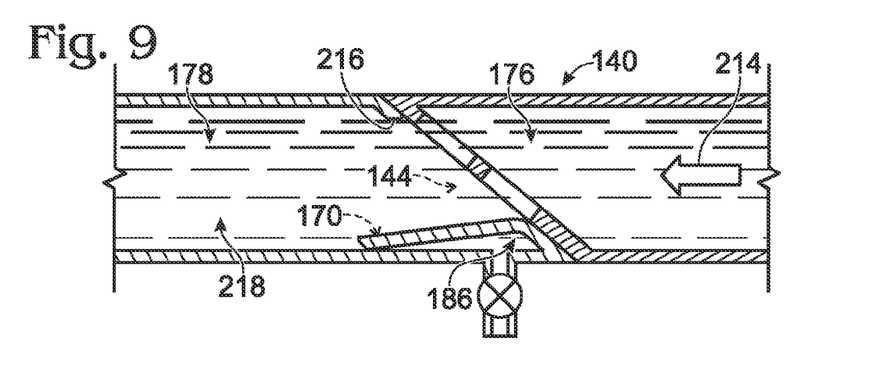
FIG. 9 is a fragmentary, longitudinal sectional view of the conduit assembly of FIG. 5 taken after rupture of the rupture valve as fluid flows through a passage created by valve rupture, from an inlet portion to an outlet portion of the conduit assembly, in accordance with aspects of the present teachings.

FIG. 9 shows conduit assembly 140 after rupture of rupture valve 144. A pressure, indicated by an open arrow at 214, exerted on rupturable element 170 from inlet portion 176 of the conduit assembly, may cause the rupturable element to fail. In particular, the rupturable element may burst because the support element is not providing support against pressure exerted on the upstream face of the rupturable element. Rupture of the rupturable element may create a passageway 216 through which fluid 218 may flow toward outlet portion 178 of the conduit assembly. Rupture of the rupturable element also may cause the rupturable element to pivot via hinge region 186 such that the rupturable element moves out of the flow path for approximate alignment with the direction of fluid flow.

Figure 10:
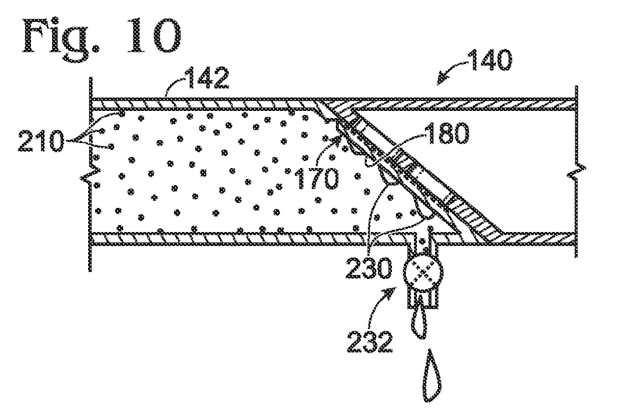
FIGS. 10 and 11 are fragmentary, longitudinal sectional views of the conduit assembly of FIG. 5, taken as in FIG. 8 during application of steam, with the conduit assembly disposed in respective horizontal and vertical orientations and with steam condensate traveling along an oblique surface of the rupture valve to a drain valve, in accordance with aspects of present teachings.
Figure 11:
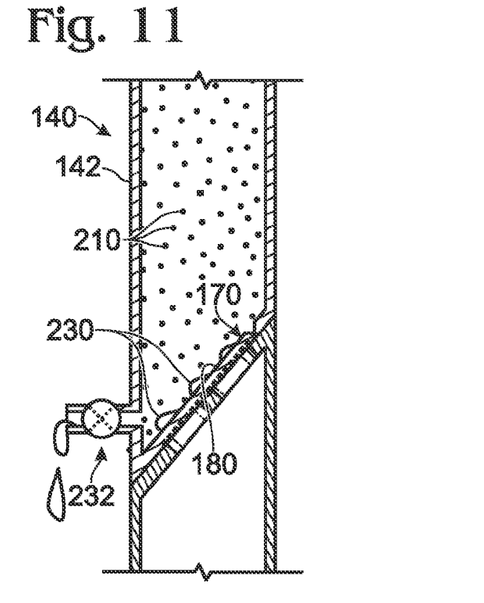

FIGS. 10 and 11 show conduit assembly 140 in respective horizontal and vertical orientations of conduit 142 during application of steam 210. The oblique arrangement of the rupture valve may direct condensate 230 toward a drain 232 in each orientation of the conduit. In particular, condensate 230 may be urged by gravity along downstream face 180 of rupturable element 170 due to its oblique disposition, whether or not face 180 is facing generally downward (FIG. 10) or generally upward (FIG. 11). A rupture valve with an oblique orientation within a conduit assembly thus may provide greater flexibility in how the conduit assembly is oriented during its use.

Example 2

Conduit Assembly with Orthogonal Rupture Valve

Figure 12:
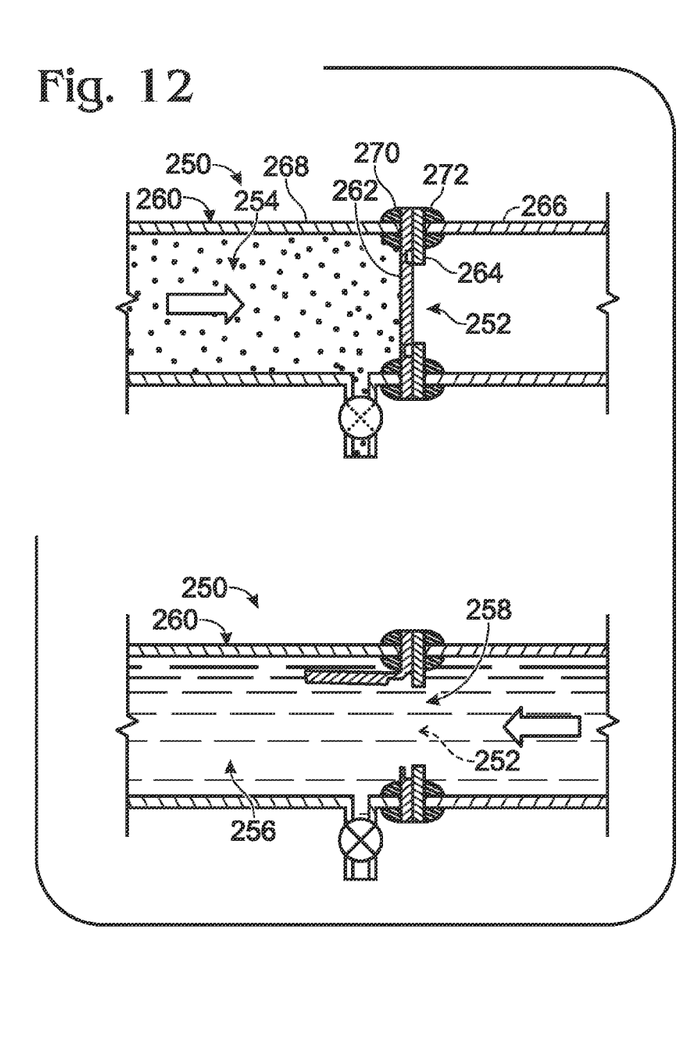
FIG. 12 is a pair of fragmentary, longitudinal sectional views of another exemplary conduit assembly taken respectively before and after rupture of a rupture valve of the conduit assembly, in accordance with aspects of the present teachings.

This example describes an exemplary conduit assembly including a conduit and a rupture valve with an orthogonal disposition within the conduit; see FIG. 12.

FIG. 12 shows another exemplary conduit assembly 250 viewed before (top) and after (bottom) rupture of a rupture valve 252 of the conduit assembly. The top panel of FIG. 12 shows conduit assembly 250 during steam sterilization of an outlet portion 254 of the assembly. The bottom panel of FIG. 12 shows the conduit assembly conducting fluid 256 through a passageway 258 created by valve rupture.

Rupture valve 252 may be arranged orthogonally relative to a conduit 260 of the conduit assembly. In particular, a rupturable element (an occlusion element) 262 and a support element 264 of the rupture valve each may define planes that are orthogonal to a flow direction through conduit 260 (and/or a long axis defined by the conduit).

The rupturable and support elements may be connected to conduit 260 by components that are separate from the conduit. For example, conduit 260 may include an upstream conduit component 266 and a downstream conduit component 268 that are attached to rupturable element 262 and support element 264 components via polymer welds 270, 272.

Example 3

Conduit Assembly with Face-to-Face Valve Elements

Figures 13, 14:
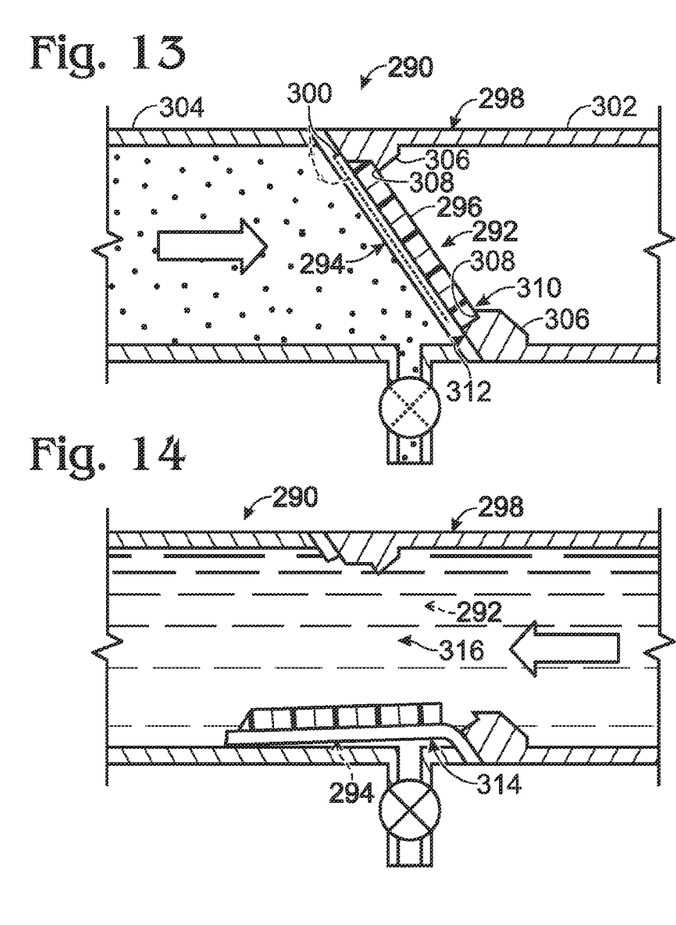
FIG. 13 is a fragmentary, longitudinal sectional view of yet another exemplary conduit assembly taken during selective application of steam to an outlet portion of the conduit assembly, in accordance with aspects of the present teachings.
FIG. 14 is a fragmentary, longitudinal sectional view of the conduit assembly of FIG. 13 taken after rupture of a rupture valve of the conduit assembly and as fluid flows through the conduit assembly, in accordance with aspects of the present teachings.

This example describes an exemplary conduit assembly 290 including a rupture valve 292 having a rupturable element 294 and a support element 296 disposed in a face-to-face relationship; see FIGS. 13 and 14.

Rupture valve 292 may have rupturable element 294 and support element 296 structured as separate components that are attached to one another, face-to-face, within a conduit 298 of the conduit assembly. The rupturable element may be a sheet of material and/or a disc that has been scored, indicated at 300, with a cut extending partway through the sheet/disc, to define a region at which the rupturable element will tear/fracture during rupture. The cut may extend adjacent the perimeter of the sheet/disc, partway (or completely) around the perimeter. The rupturable element and the support element may be held in position by the conduit. In particular, the conduit may have upstream and downstream conduit components 302, 304 that form a circumferential seal near the perimeter of the rupturable element, on respective opposing faces thereof. Furthermore, upstream conduit component 302 may project inward into the conduit channel to create a buttress structure 306 with recesses 308 for receiving and engaging the support element, as indicated at 310, and thus restricting its upstream movement. The buttress structure also may engage and support a perimeter region of the rupturable element, indicated at 312.

FIG. 13 shows conduit assembly 290 during steam sterilization. Here, rupture valve 292 is intact, with support element 296 seated against buttress structure 306.

FIG. 14 shows conduit assembly 290 after rupture valve 292 has ruptured. Here, rupturable element 294 has been torn, and both the rupturable element and the support element have pivoted together, indicated at 314, to form a passageway 316 for fluid flow through the conduit.

Example 4

Conduit Assembly with Pinch Valve

Figure 15:
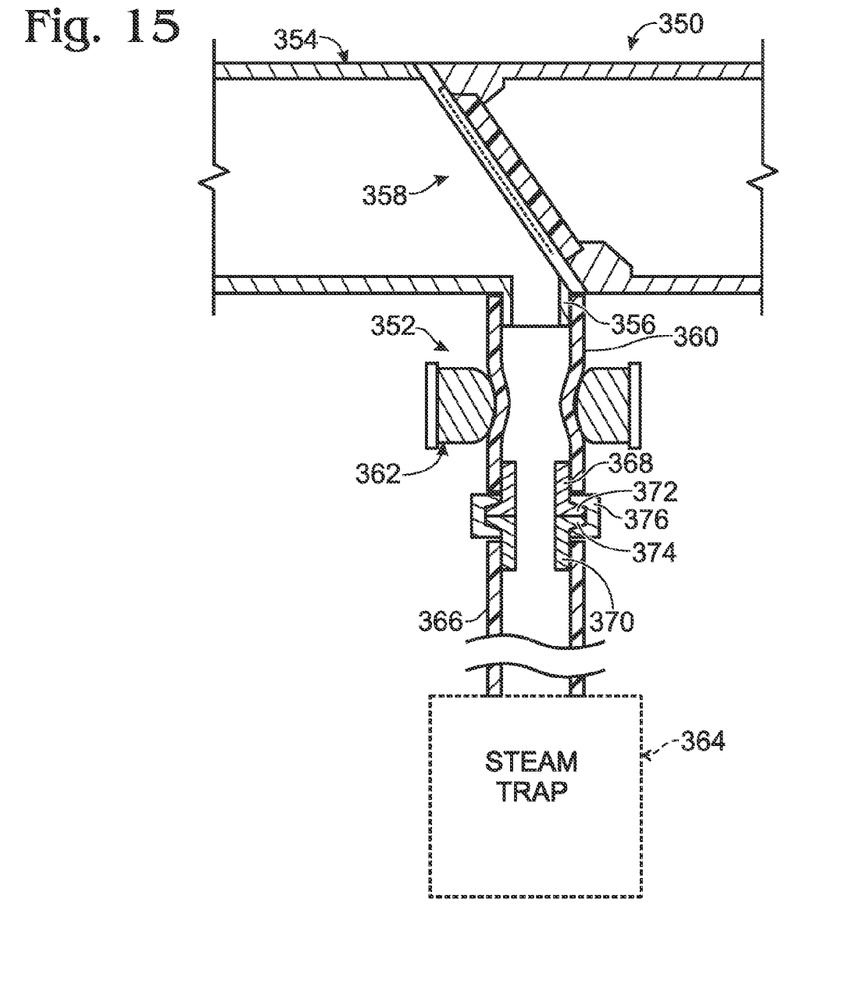
FIG. 15 is a fragmentary, longitudinal sectional view of an exemplary conduit assembly having a drain valve structured as a pinch valve created by flexible tubing and a clamp, and connected to a steam trap, in accordance with aspects of the present teachings.

This example describes an exemplary conduit assembly 350 including a drain valve 352 structured as a pinch valve; see FIG. 15.

Conduit assembly 350 may have a primary conduit 354 and an ancillary conduit 356 that branches laterally from the primary conduit. Flow through the primary conduit may be regulated by a rupture valve 358, which here is structured similarly to rupture valve 292 of Example 3.

The ancillary conduit may be configured to receive in a piece of flexible tubing 360. For example, the ancillary conduit may be a hollow tube with a nonflanged end (or a flanged end (see Example 5) or a ribbed/barbed shank, among others). The ancillary conduit may be formed unitarily with a portion of the primary conduit or may be formed separately and attached to the primary conduit after formation. Fluid flow through the ancillary conduit (and through the flexible tubing) may be controlled by a clamp 362 positioned to compress the flexible tubing, thereby forming pinch valve 352.

In some examples, the conduit assembly may be connected to a steam trap 364. The steam trap may be configured to open at appropriate times, for example, when condensate is present, and to close otherwise, to reduce unnecessary loss of steam pressure and temperature. Here, the steam trap is connected to flexible tubing 360 by additional tubing 366 via connector pipes 368, 370 having paired tri-clamp fittings 372, 374 secured with a tri-clamp 376.

Example 5

Conduit Assembly with Ancillary Conduit

Figure 16:
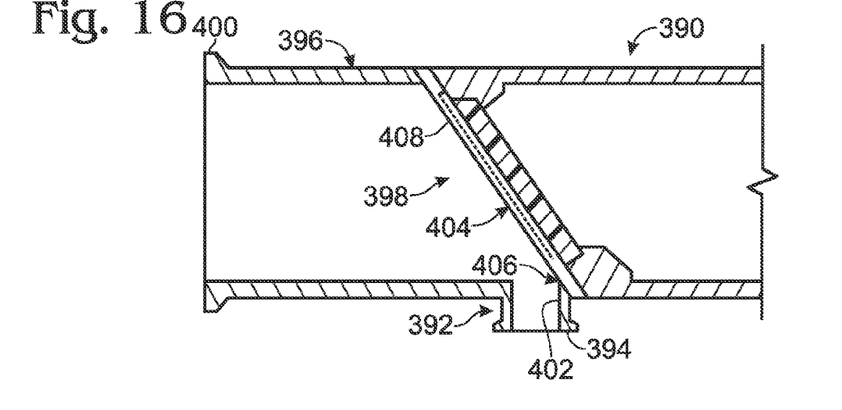
FIG. 16 is a fragmentary, longitudinal sectional view of an exemplary conduit assembly having an ancillary (drain) conduit with a tri-clamp fitting, in accordance with aspects of the present teachings.

This example describes an exemplary conduit assembly 390 having an ancillary conduit 392 with a tri-clamp fitting 394; see FIG. 16.

Conduit assembly 390 may include a main conduit 396 and a rupture valve 398 occluding the main conduit. The main conduit may have a tri-clamp fitting 400 at one or both opposing ends of the conduit. The rupture valve may be structured generally as described above in Example 3.

Ancillary conduit 392 may be positioned to receive condensate at least relatively directly from rupture valve 398. For example, the ancillary conduit made define a passage or through-hole 402 with a longitudinal location along the main conduit that overlaps the longitudinal position of the rupture valve. More particularly, a rupturable element 404 of the rupture valve may extend along a range of longitudinal positions of the main conduit, and passage 402 may be disposed adjacent an upstream/inlet end of the range of longitudinal positions. In some examples, passage 402 may at least substantially adjoin the rupturable element, indicated at 406, such that condensate may flow at least substantially directly from a downstream face 408 of the rupturable element to the passage.

Example 6

Selected Embodiments

This example describes selected embodiments of the present teachings, presented as a series of indexed paragraphs.

1. A device for controlling fluid flow, comprising: (A) a conduit defining a channel with opposing upstream and downstream directions of potential fluid flow; and (B) a rupture valve occluding the channel and being configured to resist rupture in response to pressure exerted on the rupture valve in an upstream direction and to rupture selectively in response to pressure exerted on the rupture valve in the downstream direction, the rupture valve being disposed obliquely in the channel.

2. The device of paragraph 1, wherein the rupture valve has a perimeter defining a plane, and wherein the plane is oblique to the directions of potential fluid flow.

3. The device of paragraph 1 or 2, wherein the conduit has a body that is at least substantially linear.

4. The device of paragraphs 1-3, wherein the conduit is shaped at least substantially as a hollow cylinder.

5. The device of any of paragraphs 1-4, wherein the conduit has a substantially circular cross-sectional shape.

6. The device of any of paragraphs 1-5, wherein the conduit includes a body and opposing end regions, and where at least one of the opposing end regions includes a flange extending generally outward from the body.

7. The device of paragraph 6, wherein the flange is structured as a tri-clamp fitting.

8. The device of any of paragraphs 1-7, wherein the conduit is a main conduit, further comprising an ancillary conduit branching laterally from the main conduit.

9. The device of paragraph 8, wherein the ancillary conduit includes a tri-clamp fitting.

10. The device of paragraph 8 or 9, wherein the ancillary conduit is disposed downstream of the rupture valve.

11. The device of paragraph 10, wherein the rupture valve has a downstream face disposed in a range of longitudinal positions in the conduit, wherein the ancillary conduit defines a passage, and wherein the passage has a longitudinal location along the conduit that overlaps the range of longitudinal positions.

12. The device of paragraph 11, wherein the passage at least substantially adjoins the downstream face.

13. The device of any of paragraphs 8-12, wherein fluid flow through the ancillary conduit from the channel is regulated by a lateral valve that is operatively coupled to the ancillary conduit.

14. The device of paragraph 13, wherein the lateral valve is a pinch valve.

15. The device of any of paragraphs 1-14, wherein the rupture valve includes a rupturable element and a support element disposed face to face with one another, wherein the rupturable element is configured to rupture selectively in response to pressure exerted in the downstream direction, and wherein the support element is configured to support the rupturable element such that rupture of the rupturable element is resisted in response to pressure exerted on the rupturable element in the upstream direction.

16. The device of paragraph 15, wherein the support element is configured to remain at least substantially fixed relative to the conduit when the rupturable element ruptures.

17. The device of paragraph 15 or 16, wherein the support element has opposing faces and wherein the support element defines a plurality of openings extending between the opposing faces.

18. The device of any of paragraphs 15-17, wherein the support element is connected to the rupturable element such that the rupturable element and the support element pivot together when the rupturable element ruptures.

19. The device of any of paragraphs 1-18, wherein the rupture valve is configured to remain connected to the conduit after rupture, and/or wherein the rupture valve has a predefined rupture region that is generally U-shaped.

20. The device of any of paragraphs 1-19, further comprising a filter element operatively connected to the conduit and configured to sterilize fluid flowing through the conduit.

21. A device for controlling fluid flow, comprising: (A) a conduit defining a channel with opposing upstream and downstream directions of potential fluid flow; and (B) a rupture valve occluding the conduit such that fluid flow through the conduit is restricted, the rupture valve including a rupturable element and a support element connected to one another in a face-to-face relation, such that the support element supports the rupturable element against rupture in response to pressure on the rupture valve exerted in an upstream direction and pivots with the rupturable element to permit fluid flow through the channel after the rupturable element ruptures selectively in response to pressure exerted in an downstream direction.

22. The device of paragraph 21, wherein the device includes any combination of the limitations recited above in paragraphs 2-20.

23. The device of paragraph 21 or 22, wherein the conduit defines a pair of cavities opposing one another across the rupture valve, and wherein the conduit projects inward into at least one of the pair of cavities to define a seating structure engaged by the support element and configured to selectively restrict movement of the support element in the upstream direction.

24. The device of paragraph 23, wherein the support element is flanked longitudinally within the conduit by the rupturable element and the seating structure.

25. The device of any of paragraphs 21-24, wherein the support element has a perimeter, and wherein the rupturable element extends radially beyond the perimeter for attachment to the conduit.

26. The device of any of paragraphs 21-25, wherein the rupturable element has a predefined region that is configured to be structurally weaker than other regions of the rupturable element such that the rupturable element is breached selectively in the predefined region.

27. A method of fluid transfer, comprising: (A) selecting a conduit assembly including a conduit and a rupture valve dividing a channel of the conduit into an inlet portion and an outlet portion, the rupture valve being selectively rupturable in response to pressure exerted on the rupture valve from the inlet portion; (B) applying steam to the outlet portion of the conduit with the rupture valve restricting entry of the steam into the inlet portion; and (C) rupturing the rupture valve after the step of applying with pressure exerted from the inlet portion such that fluid flows into the outlet portion from the inlet portion.

28. The method of paragraph 27, further comprising a step of connecting the conduit assembly to a closed vessel before the step of applying steam.

29. The method of paragraph 28, wherein the step of connecting includes a step of connecting the conduit assembly such that the closed vessel is farther downstream from the inlet portion than the outlet portion.

30. The method of paragraph 28 or 29, further comprising a step of steaming an interior region of the closed vessel.

31. The method of paragraph 30, wherein the step of steaming is included in the step of applying steam to the outlet portion.

32. The method of paragraph 30, wherein the step of steaming is performed before the step of applying steam to the outlet portion.

33. The method of any of paragraphs 28-32, further comprising a step of adding a fluid reagent to the closed vessel through the rupture valve, and wherein pressure exerted by the fluid reagent performs the step of rupturing.

34. The method of paragraph 33, wherein the closed vessel is a bioreactor, and wherein the step of adding includes a step of adding a medium for growing biological cells.

35. The method of paragraph 33 or 34, further comprising a step of connecting a source of the fluid reagent to the conduit assembly such that the outlet portion is farther downstream from the source than the inlet portion.

36. The method of paragraph 35, wherein the step of connecting a source is performed before the steps of applying and rupturing.

37. The method of any of paragraphs 33-36, further comprising a step of filtering the fluid reagent as the fluid reagent is flowing to the closed vessel.

38. The method of paragraph 37, wherein the step of filtering is performed upstream of the rupture valve in the conduit assembly.

39. The method of any of paragraphs 27-38, the conduit defining a long axis, wherein the step of applying is performed with the long axis disposed generally vertically.

40. The method of any of paragraphs 27-39, wherein the rupture valve includes a rupturable element connected to and occluding the conduit, and wherein the step of rupturing is performed without detaching the rupturable element completely from the conduit.

41. The method of any of paragraphs 27-40, the conduit being a main conduit, the conduit assembly also including an ancillary conduit that branches from the main conduit, further comprising a step of removing steam condensate from the main conduit via the ancillary conduit during the step of applying.

42. The method of any of paragraphs 27-41, further comprising a step of sterilizing the conduit assembly prior to the step of applying steam.

43. The method of paragraph 42, further comprising a step of connecting the conduit assembly to an upstream device, wherein the step of sterilizing includes a step of sterilizing the conduit assembly and the upstream device as a connected unit.

44. The method of paragraph 42 or 43, further comprising a step of coupling the conduit assembly to a downstream device, wherein the step of coupling is performed before the step of applying steam.

45. The method of paragraph 44, wherein the step of coupling the conduit assembly to a downstream device is performed after the step of connecting the conduit assembly to an upstream device.

The disclosure set forth above may encompass one or more distinct inventions, with independent utility. Each of these inventions has been disclosed in its preferred form(s). These preferred forms, including the specific embodiments thereof as disclosed and illustrated herein, are not intended to be considered in a limiting sense, because numerous variations are possible. The subject matter of the inventions includes all novel and nonobvious combinations and subcombinations of the various elements, features, functions, and/or properties disclosed herein.

The embodiments of the invention in which an exclusive property or privilege is claimed are defined as follows:

1. A device for controlling fluid flow, comprising:
   (a) a main conduit defining a channel having opposing upstream and downstream directions of fluid flow;
   (b) a rupture valve disposed in the channel to selectively prevent fluid flow through the channel, the rupture valve resisting rupture in response to pressure exerted on the rupture valve in the upstream direction and selectively rupturing in response to pressure exerted on the rupture valve in the downstream direction, the rupture valve extending obliquely between an upstream location and a downstream location of the channel; and
   (c) an ancillary conduit disposed downstream of the rupture valve and branching laterally from the main conduit, the ancillary conduit being in fluid communication with the channel at a location between the upstream location and the downstream location.

2. The device of claim 1, wherein the rupture valve has a perimeter defining a plane, and wherein the plane is oblique to the directions of fluid flow.

3. The device of claim 1, wherein the ancillary conduit comprises a tri-clamp fitting.

4. The device of claim 1, wherein the ancillary conduit substantially adjoins the downstream face.

5. The device of claim 1, further comprising a lateral valve operatively coupled to the ancillary conduit to selectively restrict fluid flow through the ancillary conduit from the channel.

6. The device of claim 5, wherein the lateral valve is a pinch valve.

7. The device of claim 1, wherein the rupture valve comprises:
   (a) a rupturable element having an upstream face and a downstream face; and
   (b) a support element fixedly positioned along the upstream face, wherein the rupturable element selectively ruptures in response to pressure exerted on the upstream face, and wherein the support element engages the rupturable element to prevent rupture of the rupturable element when pressure is exerted on the downstream face.

8. The device of claim 7, wherein the support element remains fixedly positioned relative to the conduit when the rupturable element ruptures.

9. The device of claim 7, wherein the support element comprises at least one aperture extending therethrough.

10. The device of claim 7, wherein the support element is connected to the rupturable element such that the rupturable element and the support element pivot when the rupturable element ruptures.

11. The device of claim 1, wherein the rupture valve has a predefined rupture region that is generally U-shaped.

12. The device of claim 1, further comprising a filter element operatively connected to the conduit and configured to sterilize fluid flowing through the conduit.

13. A device for controlling fluid flow, comprising:
   (a) a main conduit having opposing upstream and downstream directions of fluid flow;
   (b) a rupture valve disposed within the main conduit to selectively restrict fluid flow through the main conduit, the rupture valve extending between an upstream location and a downstream location, the rupture valve comprising:
      (i) a rupturable element; and
      (ii) a support element connected to the rupturable element such that the support element supports the rupturable element against rupture in response to pressure on the rupture valve exerted in an upstream direction and pivots with the rupturable element to permit fluid flow through the main conduit after the rupturable element ruptures selectively in response to pressure exerted in a downstream direction; and
   (c) an ancillary conduit disposed downstream of the rupture valve and branching laterally from the main conduit, the ancillary conduit being in fluid communication with the main conduit at a location between the upstream location and the downstream location.

14. The device of claim 13, wherein the main conduit comprises:
   (a) an upstream cavity and a downstream cavity separated by the rupture valve; and
   (b) a seating structure extending inwardly into the upstream cavity and engaging the support element to selectively restrict movement of the support element in the upstream direction.

15. The device of claim 14, wherein the support element is flanked longitudinally within the main conduit by the rupturable element and the seating structure.

16. The device of claim 13, wherein the support element has a perimeter, and wherein the rupturable element extends radially beyond the perimeter for attachment to the main conduit.

17. The device of claim 13, wherein the rupturable element has a predefined region that is configured to be structurally weaker than other regions of the rupturable element such that the rupturable element is breached selectively in the predefined region.

* * * * *